US009327005B1

(12) United States Patent
Pietrzkowski

(10) Patent No.: US 9,327,005 B1
(45) Date of Patent: May 3, 2016

(54) COMPOSITIONS AND METHODS FOR IMPROVED ENERGY METABOLISM

(71) Applicant: VDF FutureCeuticals, Inc., Momence, IL (US)

(72) Inventor: Zbigniew Pietrzkowski, Aliso Viejo, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 0 days.

(21) Appl. No.: 14/081,653

(22) Filed: Nov. 15, 2013

Related U.S. Application Data

(60) Provisional application No. 61/727,035, filed on Nov. 15, 2012.

(51) Int. Cl.
| | |
|---|---|
| *A61K 36/73* | (2006.01) |
| *A61K 33/06* | (2006.01) |
| *A61K 33/22* | (2006.01) |
| *A61K 33/42* | (2006.01) |
| *A61K 45/06* | (2006.01) |
| *A61K 47/46* | (2006.01) |

(52) U.S. Cl.
CPC .............. *A61K 36/73* (2013.01); *A61K 33/42* (2013.01); *A61K 45/06* (2013.01)

(58) Field of Classification Search
CPC ....... A61K 33/06; A61K 33/22; A61K 33/32; A61K 47/46; A61K 2236/31; A61K 2236/33; A61K 2236/331; A61K 36/73; A61K 33/42; A61K 45/06

USPC .......................................... 424/439, 714, 725
See application file for complete search history.

(56) References Cited

U.S. PATENT DOCUMENTS

| | | | |
|---|---|---|---|
| 7,629,329 B2 | 12/2009 | Lee et al. | |
| 8,252,309 B2 | 8/2012 | Gaetani | |
| 2003/0190374 A1 | 10/2003 | Howard | |
| 2006/0093685 A1* | 5/2006 | Mower et al. | 424/758 |
| 2008/0166306 A1* | 7/2008 | Eshdat et al. | 424/48 |
| 2013/0096193 A1 | 4/2013 | Kneller | |
| 2013/0131175 A1 | 5/2013 | Miller et al. | |

FOREIGN PATENT DOCUMENTS

| | | |
|---|---|---|
| EP | 1745789 A1 | 1/2007 |
| WO | 2012016018 A1 | 2/2012 |

OTHER PUBLICATIONS

American Nutrition at http://www.american-nutrition.com/rockland.html, Jun. 30, 2007.*
Herda, T.J., et al., "Effects of a Supplement Designed to Increase ATP Levels on Muscle Strength, Power Output, and Endurance," Journal of the International Society of Sports Nutrition, Jan. 29, 2008, 5 pages.

* cited by examiner

*Primary Examiner* — Blessing M Fubara
(74) *Attorney, Agent, or Firm* — Fish & Tsang LLP

(57) ABSTRACT

Compositions and methods for dietary supplements that contain a cold-water extract of humic shale and/or an extract of the apple fruit or skin of the apple fruit that is/are effective to modulate in vivo cytokines, oxygen consumption rate, extracellular acidification rate, and ATP production.

13 Claims, 5 Drawing Sheets

COMPOSITIONS AND METHODS FOR IMPROVED ENERGY METABOLISM

This application claims priority to our U.S. provisional application with the Ser. No. 61/727,035, which was filed 15 Nov. 2012. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is compounds, compositions, and methods for improvement of energy metabolism, and particularly ATP production, oxygen utilization rate, and extracellular acidification rate.

BACKGROUND OF THE INVENTION

The following description includes information that may be useful in understanding the present invention. It is not an admission that any of the information provided herein is prior art or relevant to the presently claimed invention, or that any publication specifically or implicitly referenced is prior art.

Energy metabolism and ATP production is closely linked to oxygen utilization, which is best illustrated when comparing the energy balances of aerobic and anaerobic glucose utilization. Under aerobic oxidative conditions, glucose is completely metabolized to $CO_2$ and $H_2O$, yielding 34 mol ATP/mol glucose, whereas under anaerobic, oxygen depleted conditions, glucose is incompletely metabolized to lactic acid yielding only 2 mol ATP/mol glucose.

Unfortunately, there are numerous conditions and circumstances under which organs and tissues can experience oxygen partial pressures that are less than ideal. Moreover, there are also various conditions and circumstances under which organs and tissues are not fully capable of utilizing oxygen, even when oxygen is present at relatively high partial pressure. Still further, reduced oxygen utilization may also reduce ATP production, potentially leading to loss in muscular strength, power output, and endurance. ATP production may also be impaired in various disorders and malnutritive states, again leading to a significant reduction of muscular strength, loss of proper function, and fatigue. To help improve oxygen utilization in an organism, supplemental oxygen can be provided via inhalation. However, such supplementation is often impractical.

In order to increase ATP levels, various nutritional supplements are known in the art that rely on creatine compounds. Creatine has been reported to be effective in stimulation of ATP generation due to its role in anaerobic production of ATP during short/intensive exertions via the creatine kinase system. For example, US 2013/0131175 and US 2013/0096193 teach use of such compositions, while more complex creatine compositions are reported in U.S. Pat. No. 8,252,309. However, such supplements often fail to produce the desired increase in ATP production, and particularly ATP production in muscle.

In other known approaches, precursors for ATP synthesis were reported to increase ATP as can be taken from EP 1745789. However, such strategy may not be fully successful as is discussed in J Int Soc Sports Nutr. 2008; 5: 3 (Effects of a supplement designed to increase ATP levels on muscle strength, power output, and endurance) for a supplement where adenylpyro-phosphoric acid and calcium pyruvate were administered and where no differences were found in actual exercise parameters. To overcome potential issues with inefficient synthesis or uptake of precursors, ATP can be directly administered using enteric coating to a mammal as described in U.S. Pat. No. 7,629,329. However, hydrolysis in the gut and extracellular space is likely to negate all of the purported benefits. Moreover, ATP is a charged compound at physiological pH and is as such unlikely to pass cell membranes in significant quantities to provide intracellular ATP.

In still another approach, as shown in WO 2012/016018, the water-extractable fraction of a complex fermentation product of various plant materials was reported to increase oxygen consumption rate and intracellular ATP production, while in another approach, certain silica hydride minerals were reported to indirectly increase ATP as described in US 2003/0190374. Such compositions may be effective to at least some degree, however, may be subject to stability issues or difficulties in sourcing raw materials.

Therefore, while numerous compositions and methods of increasing energy metabolism and ATP production are known in the art, all or almost all of them suffer from one or more disadvantages. Thus, there is still a need to provide improved compositions and methods for increasing energy metabolism and ATP production.

SUMMARY OF THE INVENTION

The inventive subject matter is drawn to compositions and methods of modulating energy metabolism, and especially to nutritional supplements and dietary compositions that significantly increase ATP production and oxygen utilization. Most remarkably, contemplated compositions and methods utilize the combination of one or more minerals, which may be fortified with a fruit extract to substantially increase blood ATP and subjective energy level. Even more unexpectedly the inventor discovered that the increase in ATP production was even more pronounced (relative to the increase in blood) in skeletal muscle tissue.

In one aspect of the inventive subject matter, a method of increasing ATP in a tissue having mitochondria (e.g., whole blood or muscle tissue) is contemplated in which in one step a mineral composition is provided that has a pharmaceutically or nutritionally acceptable carrier in combination with a combination of trace elements in ionic or elemental form. Most preferably, the trace elements are in the composition in an amount proven to increase ATP quantities in a tissue upon oral administration of the mineral composition, and the mineral composition is administered under a protocol demonstrated to increase the ATP in the tissue.

In some aspects, the trace elements are selected from the group consisting of Beryllium, Boron, Cadmium, Cobalt, Dysprosium, Erbium, Europium, Gadolinium, Holmium, Lithium, Lutetium, Magnesium, Manganese, Nickel, Rhenium, Samarium, Sodium, Terbium, Ytterbium, Yttrium, and Zinc, while in other aspects the trace elements are selected from the group consisting of Boron, Lanthanum, Magnesium, sodium, and Strontium. In further aspects, the trace elements are selected from the group consisting of Aluminum, Beryllium, Calcium, Cobalt, Copper, Erbium, Europium, Gadolinium, Hafnium, Holmium, Iron, Lutetium, Manganese, Nickel, Palladium, Phosphorus, Samarium, Terbium, Thorium, Thulium, Ytterbium, Yttrium, and Zinc. Viewed from a different perspective, the combination of trace elements may also comprise an (e.g., aqueous) extract of humic shale, which may or may to be dried. Additionally, the mineral composition may further comprise a fruit extract that includes polyphenolic compounds, and most preferably an extract of apple fruit or apple skin.

Therefore, the inventors also contemplate a mineral composition that comprises a pharmaceutically or nutritionally acceptable carrier in combination with a combination of trace elements in ionic or elemental form, wherein the trace elements are in the composition in an amount proven to increase ATP quantities in a tissue (e.g., whole blood or muscle tissue) upon oral administration of the mineral composition. With respect to the trace elements, the same considerations as provided above apply. Moreover, contemplated compositions may further include a fruit extract that is enriched in polyphenolic compounds (e.g., apple extract or apple skin extract).

In another aspect of the inventive subject matter, the inventor also contemplates a method of identifying a mineral composition as increasing ATP production in a tissue. Especially preferred methods include a step of combining a mineral composition with whole blood to form an incubation mixture, and a further step of lysing the whole blood in the incubation mixture, and combining the lysed whole blood with a luciferase to form a reaction mixture. In yet another step, light output of the reaction mixture is measured (e.g., for at least 10 minutes), and the light output is compared against a standard, wherein increased light output over the standard is indicative of an increase of ATP production by the mineral composition.

Most preferably, the mineral composition in such methods comprises at least one element selected from the group consisting of Beryllium, Boron, Cadmium, Cobalt, Dysprosium, Erbium, Europium, Gadolinium, Holmium, Lithium, Lutetium, Magnesium, Manganese, Nickel, Rhenium, Samarium, Sodium, Terbium, Ytterbium, Yttrium, and Zinc, or comprises an aqueous extract of humic shale.

Various objects, features, aspects and advantages of the inventive subject matter will become more apparent from the following detailed description of preferred embodiments.

DETAILED DESCRIPTION

Figure 1:
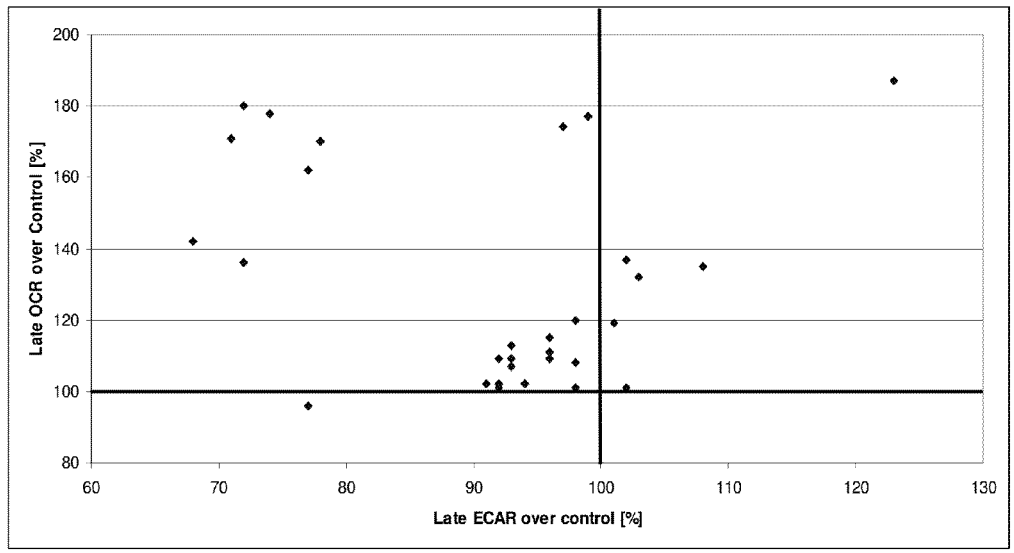
FIG. 1 is a graph depicting OCR and ECAR data in cells exposed to contemplated compositions.

The inventor has now unexpectedly discovered that selected nutritionally acceptable compositions are effective to improve various aspects of energy metabolism, and especially oxygen utilization, extracellular acidification rate, and/or ATP production. It should be especially appreciated that the compositions according to the inventive subject matter do not affect in vivo levels of reactive oxygen species and pO2, despite the increased ATP production. Additionally, the inventors also observed in at least some experiments that certain cytokines (IFN-alpha) were increased in vivo and certain chemokines (MCP-1) decreased in vivo upon oral administration of contemplated compositions.

Particularly preferred compositions comprise a cold-water extract of humic shale and/or an extract of the apple fruit or skin of the apple fruit. Most preferably, the extract(s) are admixed with a nutritionally acceptable carrier to so form a dietary supplement or food item. It is further generally preferred that the extract(s) is/are present in the nutritional supplement or food item in an amount effective to provide desirable effects on energy production, and especially oxygen utilization, extracellular acidification, and/or ATP production.

Remarkably, oral administration of contemplated compositions increased the blood level of total ATP, with no concomitant increase in blood ROS or serum lactate. Even more notably, the inventor discovered that oral administration of contemplated compositions increased the level of total ATP in muscle tissue several-fold (over the blood level). Interestingly, total mTOR levels in blood were found to be reduced due to the treatment under these experimental conditions, while blood glucose was not significantly changed. Additionally, supplements and food items contemplated herein may increase (upon oral administration) in vivo oxygen consumption rate, decrease extracellular acidification rate, and/or increase intracellular ATP production. In further aspects of the inventive subject matter, contemplated compositions will also be effective in vivo upon oral administration to increase certain cytokines (IFN-alpha) and to decrease certain chemokines (MCP-1).

With respect to desirable quantities, it is generally contemplated that all quantities are suitable that provide a measurable effect in vivo upon oral administration. Consequently, suitable quantities are those that are effective to increase oxygen consumption rate, decrease extracellular acidification rate, increase a ratio of oxygen consumption rate to extracellular acidification rate, and that increase the intracellular ATP production (in blood and/or muscle). For example, the extract(s) is/are present in the dietary supplement or food item in an amount of at least 1-5 wt %.

Consequently, the inventors also contemplate a method of modulating energy metabolism in a mammal, in which in one step a (preferably cold-water) extract of humic shale and/or an extract of the apple fruit or skin of the apple fruit is provided. In another step, the extract(s) is/are combined with a nutritionally acceptable carrier in an amount effective to increase oxygen consumption rate, to decrease extracellular acidification rate, to increase a ratio of oxygen consumption rate to extracellular acidification rate, and/or to increase the intracellular ATP production (in blood and/or muscle), to thereby produce a nutritional supplement. In still another step, the nutritional supplement is provided to the mammal in an amount effective to modulate the energy metabolism and/or cytokine production in the mammal. As before, contemplated methods will also be effective to increase certain cytokines (IFN-alpha) and to decrease certain chemokines (MCP-1).

Therefore, in yet further contemplated aspects, modulation of energy metabolism in a mammal is deemed effective to increase exercise capacity or strength, to reduce adverse effects due to rapid altitude change, to increase memory function, and/or to alleviate a symptom associated with a respiratory condition.

The inventors have also discovered that various nutritionally acceptable compositions and methods not only significantly improve oxygen utilization in a mammal, but may also modulate certain cytokine and chemokine profiles in vivo. Preferably, compositions contemplated herein are orally administered in combination with a nutritionally acceptable liquid or solid carrier. Among other desirable effects, compositions and methods presented herein are thought to significantly increase oxygenation of blood in vivo, increase intracellular ATP levels in vivo (in blood and/or muscle), increase oxygen consumption rate (OCR) in vivo, decrease extracellular acidification rate (ECAR), substantially increase the ratio of OCR/ECAR, stimulate anti-inflammatory cytokines and/or suppress pro-inflammatory chemokines.

Based on the below data and additional considerations, the inventor contemplates that compositions and methods presented herein may also be useful in modulating energy metabolism in a mammal. Consequently, it is also contemplated that the compositions and methods herein are useful in producing an increase in OCR, a decrease in ECAR, an increase in the ratio of OCR/ECAR, an increase in intracellular ATP levels, and/or an increase in intracellular oxygen utilization. Viewed from a different perspective, it should be appreciated that the compositions and methods presented herein allow for more efficient use of existing oxygen from the cellular milieu, and/or a mode in which cells are activated to utilize more oxygen.

Therefore, it is contemplated that the compositions according to the inventive subject matter will be useful in the treatment of various signs and symptoms of conditions associated with a reduction in oxygen utilization. For example, it is contemplated that the compositions may be useful in the treatment (e.g., to provide symptomatic relief or subjective well being, or to increase OCR, decrease ECAR, etc.) of adverse effects due to rapid altitude change (e.g., change in altitude of at least 2000 ft in less than 24 hrs), or of symptoms of a respiratory condition (e.g., due to chronic obstructive pulmonary disease, bronchitis, asthma, emphysema, tobacco use, autoimmune disorder, obesity, air pollution, etc.). Contemplated compositions may be especially useful in increasing cerebral oxygen utilization and thus be suitable to increase memory function (e.g., executive functions, cognitive functions, etc.). Still further, contemplated compositions may also be advantageous in restoration of and/or increase of exercise capacity in sports or in daily activities, increase in VO2 max (maximal oxygen consumption, aerobic capacity), and endurance, as well as in a delay in onset of anaerobic metabolism under strain.

It should still further be appreciated that contemplated compositions and methods increase the intracellular ATP concentration without substantial generation (i.e., less than 10%, and more typically less than 5% as compared to pre-administration) of various radical species, and especially without increased production of reactive oxygen species (ROS) and hydroxyl radicals. Such finding is particularly noteworthy as an increase in endogenous (intracellular) ATP is typically associated with an increase in intracellular free radicals. In this context, it should be appreciated that cells function differently at high intracellular ATP levels without free radicals as compared to low levels of intracellular ATP. In case of blood cells such difference is particularly important (e.g., different activities of lymphocytes form multiple sclerosis patients due to different intracellular ATP concentration). Moreover, and as also provided in more detail below, the inventor discovered that compositions contemplated herein significantly increase ATP levels in muscle tissue.

Therefore, especially contemplated uses also include those where an increase in intracellular respiration activity would be particularly desirable or beneficial (e.g., muscle performance and endurance, delay of aging, MS, cancer, skin aging/senescence, hypoxia, ischemia, cardiovascular, autoimmune, immunological responsiveness, metabolism including appetite control and CNS function, and others). Likewise, especially contemplated uses also include those where conditions related to reduced oxygen levels in blood are encountered (e.g., systemic depressed respiration, COPD, asthma, bronchitis, etc.)

Additionally, and especially where individual compounds ('actives') are isolated from the compositions presented herein, such individual compounds may be administered in various medical uses, and especially in surgical interventions where hypoxia is commonly encountered (e.g., open heart surgery, organ transport and/or transplantation, induced hypothermia after traumatic brain injury, etc.).

Particularly preferred compositions and methods are exemplarily provided in the experimental section below. However, it should be appreciated that numerous modifications may be made to the compositions and methods without departing from the inventive concept presented herein. Consequently, a method of modulating energy metabolism in a mammal (e.g., human, but also a pet, a livestock/farm animal, or a zoo animal) is generally contemplated in which in one step a cold-water extract of humic shale and/or an extract of the apple fruit or skin of the apple fruit is provided. In another optional step, the extract(s) is/are then combined with a nutritionally acceptable carrier to so form a nutritional supplement or food item. In yet another step, the cold-water extract of humic shale and/or extract of the apple fruit or skin of the apple fruit, is then provided (with or without carrier) to a mammal in an amount effective to modulate energy metabolism in the mammal and/or modulate cytokine/chemokine profile in the mammal.

With respect to the cold-water extract of humic shale it should be appreciated that there are numerous alternative materials that are also deemed effective for use herein. For example, it is contemplated that alternative materials may be hot-water extracts of humic shale, or extracts of humic shale prepared using solvents other than water. For example, shale may be extracted with solvent mixtures, which will typically (but not necessarily) include water, and especially suitable solvents include nutritionally acceptable solvents (e.g., various alcohols, ethers, esthers, oils, etc.), and all reasonable mixtures thereof.

Moreover, it should still further be appreciated that while humic shale is particularly preferred, other humic and fulvic materials are also deemed suitable. For example, contemplated materials include those that can be extracted from soil and sediments, and most preferably from soil and sediments that previously contained lignocellulosic materials or into lignocellulosic materials were previously introduced. Consequently, suitable materials may be geologicaly recent or relatively ancient. Regardless of the age, it is generally preferred that the extracts from such materials may be prepared in numerous manners, and particularly by aqueous alkaline extraction. Therefore, and depending on the particular extraction process and pH used, these materials may be employed as a source for humic acids and/or fulvic acids. Typical isolation protocols are provided by Swift, R. S. 1996 Organic matter characterization (chap 35). pp. 1018-1020, in D. L. Sparks et al. (eds) Methods of soil analysis. Part 3. Chemical methods.

Soil Sci. Soc. Am. Book Series: 5. Soil Sci. Soc. Am. Madison, Wis., which is incorporated by reference herein.

In still further contemplated aspects it should be noted that the extracts may also be prepared from degradation products of various lignocellulosic materials and even biosolids. For examples, such materials may be subjected to biodegradation using suitable microorganisms. Alternatively, or additionally, such materials may be chemically and/or thermally treated (e.g., using oxidative degradation in a medium containing high concentrations of ferric ions, and/or dry heat or steam treatment) to form a precursor materials that is then extracted. Alternatively, there are already numerous commercially available sources of humic/fulvic acid extracts, and all of them are deemed suitable for use herein.

With respect to humic shale materials, the inventor unexpectedly discovered that not all materials will provide extracts with identical properties, even where the humic shale materials are taken from the same geological area. Indeed, the inventor noted that certain geologic strata at the same location were even inhibitory (with respect to ATP stimulation) while other strata had a strong ATP generating effect as is shown in more detail below. Consequently, the inventors contemplate that selected minerals or mineral compositions may be particularly effective in generating ATP stimulation in blood and/or muscle tissue. Therefore, especially contemplated compositions not only include complex mineral mixtures as those found in the aqueous extracts of humic shale, but also processed extracts, and even mineral mixtures compounded from relatively pure minerals and/or mineral salts. For example, contemplated compositions will include those that have at least one, and more typically at least two of the minerals listed in Table 1 below. Table 1 lists the exemplary composition of an aqueous extract of humic shale after drying with all values provided in mg/kg of the dried extract. Most typically, the mineral(s) will be present as soluble salt(s), but may also be present in non-ionic form (e.g., in metallic form).

TABLE 1

| Element | Batch 1 | Batch 2 | Batch 3 |
|---|---|---|---|
| Aluminum (Al) | 22,600 | 25,000 | 16,700 |
| Antimony (Sb) | 1.79 | 1.44 | 0.789 |
| Arsenic (As) | 1.545 | 0.719 | 0.677 |
| Barium (Ba) | <0.5 | <0.5 | <0.5 |
| Beryllium (Be) | 6.07 | 6.75 | <0.5 |
| Bismuth (Bi) | <0.5 | 20.08 | 4.8 |
| Boron (B) | 24 | 33.27 | 40.7 |
| Cadmium (Cd) | 9.911 | 6.653 | 6.561 |
| Calcium (Ca) | 9,960 | 13,810 | 12,500 |
| Carbon (C) | <2,000 | <2,000 | 2,000 |
| Cerium (Ce) | 14.2 | 11.458 | 6.99 |
| Cesium | 0.093 | 0.127 | <0.5 |
| Chloride (Cl-) | 3,098 | 2,583 | N.D |
| Chromium (Cr) | 2.87 | 3.69 | <0.5 |
| Cobalt (Co) | 92.9 | 93.74 | 71.2 |
| Copper (Cu) | 8.18 | 5.69 | <0.5 |
| Dysprosium (Dy) | 12.9 | 9.75 | 7.16 |
| Erbium (Er) | 5.82 | 4.63 | 3.35 |
| Europium (Eu) | 2.53 | 2.04 | 1.25 |
| Fluoride (F-) | 10 | 40 | 18 |
| Gadolinium (Gd) | 11.4 | 8.65 | 6.57 |
| Gallium (Ga) | 0.23 | 0.23 | 0.66 |
| Germanium (Ge) | 0.119 | 0.102 | <0.5 |
| Gold (Au) | 5.93 | 5.97 | 7.89 |
| Hafnium (Hf) | 0.409 | 0.397 | <0.5 |
| Holmium (Ho) | 2.42 | 1.89 | 1.39 |
| Indium (In) | 0.022 | 0.054 | <0.5 |
| Iodine (I-) | 40 | 30 | 35 |
| Iridium (Ir) | 0.002 | 0.003 | <0.5 |
| Iron (Fe) | 443 | 492 | 143 |
| Lanthanum (La) | 4.35 | 5.55 | <0.5 |
| Lead (Pb) | 0.121 | 0.148 | 0.106 |

TABLE 1-continued

| Element | Batch 1 | Batch 2 | Batch 3 |
|---|---|---|---|
| Lithium (Li) | 376 | 368 | 599 |
| Lutetium (Lu) | 0.447 | 0.376 | <0.5 |
| Magnesium (Mg) | 96,200 | 105,500 | 118,000 |
| Manganese (Mn) | 1,260 | 1,180 | 1,090 |
| Mercury (Hg) | <0.001 | 0.336 | <0.001 |
| Molybdenum (Mo) | <0.5 | <0.5 | 4.8 |
| Neodymium (Nd) | 17.1 | 15.7 | 8.46 |
| Nickel (Ni) | 326 | 261.3 | 248 |
| Niobium (Nb) | 0.381 | 0.59 | 0.562 |
| Nitrogen (N) | <2,000 | <2,000 | <2,000 |
| Osmium (Os) | 0.011 | 0.013 | <0.5 |
| Palladium (Pd) | 0.571 | 0.44 | <0.5 |
| Phosphorus (P) | 7.18 | 88.92 | <0.5 |
| Platinum (Pt) | 0.003 | 0.004 | <0.5 |
| Potassium (K) | 469 | 850 | 1,090 |
| Praseodymium (Pr) | 2.59 | 2.41 | 1.3 |
| Rhenium (Re) | 0.073 | 0.114 | <0.5 |
| Rhodium (Rh) | 0.004 | 0.09 | <0.5 |
| Rubidium (Rb) | 3.34 | 4.752 | 3.34 |
| Ruthenium (Ru) | <0.001 | <0.001 | <0.5 |
| Samarium (Sm) | 8.41 | 6.72 | 4.13 |
| Scandium (Sc) | 3.16 | 2.51 | 1.53 |
| Selenium (Se) | <0.5 | 7.85 | 4 |
| Silicon (Si) | 894 | 1,100 | 470 |
| Silver (Ag) | <0.5 | <0.5 | <0.5 |
| Sodium (Na) | 36,700 | 41,300 | 40,900 |
| Strontium (Sr) | 39.5 | 98.89 | 172 |
| Sulfur (S) | 223,000 | 223,000 | 233,000 |
| Tantalum (Ta) | 0.085 | 0.072 | <0.5 |
| Tellurium (Te) | 1.85 | 1.98 | 1.07 |
| Terbium (Tb) | 2.35 | 1.801 | 1.26 |
| Thallium (Tl) | <0.5 | <0.5 | <0.5 |
| Thorium (Th) | 1.6 | 1.31 | 0.481 |
| Thulium | 0.66 | 0.509 | <0.5 |
| Tin (Sn) | <0.001 | <0.5 | 0.205 |
| Titanium (Ti) | <0.5 | 2.62 | <0.5 |
| Tungsten (W) | 0.159 | <0.5 | <0.5 |
| Vanadium (V) | <0.5 | 22.7 | <0.5 |
| Ytterbium (Yb) | 3.65 | 2.794 | 2.02 |
| Yttrium (Y) | 125 | 88.97 | 77.5 |
| Zink (Zn) | 458 | 467 | 341 |
| Zirconium (Zr) | 5.1 | 4.71 | 9.81 |

As is also provided in more detail below, it should be noted that the biological activity of contemplated compositions can be readily established by various manners, and particularly preferred manners include incubation of whole blood in vitro with contemplated compounds, followed by analysis. As such, preferred selections of the individual elements in the composition can be done on a rational basis. Such selection may therefore be a selection of a particular geologic stratum, or selection of certain elements in metallic or ionic form for use in the composition. Where desired, the selection can then be confirmed in vivo using blood or muscle tissue as sample after oral administration of the composition. Moreover, the inventors have also discovered that pH may be a possible identifier for biological activity of aqueous extracts, and in at least some cases (using humic shale as starting material) noted that most active crude extracts had an acidic pH, typically at about 3.5. While aqueous extracts are generally deemed useful, it is typically preferred that the extracts are dried, and most preferably heat dried or spray dried.

Similarly, with respect to the extract of the apple fruit or skin of the apple fruit it is generally preferred that the extract is an ethanolic extract of the apple fruit, most preferably in powder form. While not limiting to the inventive subject matter, it is contemplated that the apple extract may at least in part derive its activity from polyphenolic compounds present in the apple skin. Therefore, it should be appreciated that numerous other plant extracts are also deemed appropriate and especially contemplated plants will include those with a relatively high (poly)phenolic content, including acai, chokeberry, currant, bilberry, blueberry, etc. Likewise, suitable plant materials for extraction also include grape (and especially grape seed), strawberry, tea leaves, etc. to provide significant quantities of proanthocyanidins, catechins, resveratrol, quercetin, etc. Alternatively, or additionally, contemplated extracts need not be ethanolic extracts, but may also be aqueous extracts, or crude extracts that are further refined to enrich the extract in one or more desirable fraction.

Regardless of the manner of preparation of the extract(s), it is generally preferred that the extract(s) is/are then combined (after optional processing) with a nutritionally acceptable carrier to so form a dietary supplement or food item. For example, suitable liquid carriers include water, tea, coffee, fruit juices, etc. Suitable solid carriers include snack bars, cereal and cereal products, dairy product, backed goods, etc. Combination may be performed at the time of manufacture, or by the user (preferably using previously measured or prepackaged amounts of the extract(s)). Depending on the particular use, it should be appreciated that the extract(s) may be present in the dietary supplement/food item in varying amounts. However, it is generally preferred that the extract(s) is/are present in a combined amount of at least 0.01 wt %, more typically at least 0.1 wt %, even more typically at least 1 wt %, and most typically at least 5 wt %. Thus, and viewed from a different perspective, the extract(s) may be present in the nutritional supplement in amount effective to increase an interleukin, decrease a chemokine, increase oxygen consumption rate, decrease extracellular acidification rate, increase a ratio of oxygen consumption rate to extracellular acidification rate, and/or to increase the intracellular ATP production.

In still further contemplated aspects, it should be appreciated that the compositions presented herein may be further combined with one or more ingredients having the same, overlapping, or additional desirable effects on energy metabolism and/or cytokine/chemokine levels, and all such known compositions are deemed suitable for use herein. For example, suitable additional ingredients include various plant- and/or protein-based materials. For example, additional ingredients include beet extracts, chromium compounds, boron-containing compounds, etc.

Exemplary compositions therefore include liquid and solid compositions that include one, two, three, four, five, or more elements found in humic shale in ionic and/or elemental form in an amount effective to increase ATP in whole blood and/or muscle tissue when orally administered to an individual. For example, suitable elements include one or more of Aluminum (Al), Antimony (Sb), Arsenic (As), Barium (Ba), Beryllium (Be), Bismuth (Bi), Boron (B), Cadmium (Cd), Calcium (Ca), Cerium (Ce), Cesium (Cs), Chloride (Cl-), Chromium (Cr), Cobalt (Co), Copper (Cu), Dysprosium (Dy), Erbium (Er), Europium (Eu), Fluoride (F-), Gadolinium (Gd), Gallium (Ga), Germanium (Ge), Gold (Au), Hafnium (Hf), Holmium (Ho), Indium (In), Iodine (I-), Iridium (Ir), Iron (Fe), Lanthanum (La), Lithium (Li), Lutetium (Lu), Magnesium (Mg), Manganese (Mn), Molybdenum (Mo), Neodymium (Nd), Nickel (Ni), Niobium (Nb), Osmium (Os), Palladium (Pd), Phosphorus (P), Platinum (Pt), Potassium (K), Praseodymium (Pr), Rhenium (Re), Rhodium (Rh), Rubidium (Rb), Ruthenium (Ru), Samarium (Sm), Scandium (Sc), Selenium (Se), Silicon (Si), Silver (Ag), Sodium (Na), Strontium (Sr), Sulfur (S), Tantalum (Ta), Tellurium (Te), Terbium (Tb), Thallium (Tl), Thorium (Th), Thulium (Tm), Tin (Sn), Titanium (Ti), Tungsten (W) Vanadium (V), Ytterbium (Yb), Yttrium (Y), Zinc (Zn), and Zirconium (Zr). For example, contemplated compositions will have one or two or more of the above elements, and contemplated compositions include crude aqueous extracts and powders from such extracts containing all of the above elements, as well as liquids and solid compositions containing subsets of the above elements. Thus, compositions comprising one or more of Beryllium, Boron, Cadmium, Cobalt, Dysprosium, Erbium, Europium, Gadolinium, Holmium, Lithium, Lutetium, Magnesium, Manganese, Nickel, Rhenium, Samarium, Sodium, Terbium, Ytterbium, Yttium, and Zinc are contemplated. Similarly, contemplated compositions may also comprise Boron, Cadmium, Lanthanum, Magnesium, Sodium, and/or Strontium.

In further preferred aspects, the compositions contemplated herein will preferably include the elements in ratios that are similar to those found in the humic shale, or humic shale extract. However, it should be noted that the elements may also be present in ratios other than those provided above, and all ratios that are effective in raising ATP production (particularly in muscle tissue) are deemed suitable for use herein. Most typically, contemplated compositions will comprise at least 1 mg, more typically at least 10 mg, and even more typically at least 100 mg of the elements in a single oral dosage form. Thus, typical dosage forms will comprise between 1-10 mg, between 10-100 mg, between 100-500 mg, between 500-1,000 mg, and even more of the elements.

Experimental Data

Pilot Studies

Materials:

Powdered cold-water extract of humic shale and powdered ethanolic extract of apple fruit skin are commercially available products (Elemin™ (cold water extract of senorian trace minerals, N881.1), and FC27, respectively) and were provided by FutureCeuticals, Inc., Momence, Ill. USA. Dulbecco's phosphate buffered saline (PBS) and water was purchased from Sigma Chem. Co. (St Louis, Mo., USA). Protein Low Binding microtubes were obtained from Eppendorf (Hauppauge, N.Y., USA) and RC DC Protein Assay Kit II was purchased from Bio-Rad (Palo Alto, Calif., USA). ADP-kinase kits were from Promega (Madison, Wis., USA), intracellular ROS and iso-PGF2-α assay kits were purchased from Cell Biolabs (San Diego, Calif., USA). ATP-luciferase assay was obtained from Calbiochem (San Diego, Calif., USA). Heparin and "dry" blood collection tubes were obtained from BD Vacutainer (Franklin Lakes, N.J., USA).

Clinical Study:

Thirty six adult volunteers with informed consent were recruited for the study. All study subjects are generally healthy and not using any type of medication or supplements for a period of 15 days prior to the start of the study. The criteria of selection included their age (>25 and <45 years) with a BMI>21 and <30 kg/m$^2$ (overweight and moderately obese), with a mean BMI of 26.43 (SD 3.035). Subjects were free of rhinitis, influenza and other infections, non diabetic and generally free of allergies to dietary products. Subjects using anti-inflammatory, anti-pain medications, statins or anti-diabetic drugs, anti-allergic medicines, multivitamins or supplements rich in polyphenols were excluded. Subjects were fasted for 12 h prior to the initial blood draw. Groups of 12 subjects (each containing six males and six females per group) were randomly selected from the pool to receive: a.) one encapsulated dose of placebo (empty capsules) (Group 1); or, b.) 150 mg of encapsulated powder comprising the cold-water extract of humic shale and/or extract of the apple fruit or skin of the apple fruit (group 2); or, c.) 150 mg of the cold-water extract of humic shale and/or extract of the apple fruit or skin of the apple fruit in 100 mL of water (Group 3).

Subjects in Groups 1 and 2 were administered 100 ml water to match the amount of water ingested by subjects in Group 3. Body temperature and blood samples were taken prior to and after treatment. Blood samples were collected every thirty minutes after treatment in heparinized tubes and snap frozen to preserve ATP and ROS integrity. Lactate, partial pressure of oxygen (P02) and oxygen saturation (sO2) were measured with a portable clinical blood analyzer unit (i-STAT Portable Clinical Blood Analyzer, Abbott Laboratories, NJ USA).

Blood Collection:

Before samples were orally ingested, blood was collected at Time Zero (T0). For each participant two 9 mL blood samples were drawn from an antecubital vein: one tube contained lithium-heparin as an anticoagulant, the other was anticoagulant-free. Following Time Zero, blood was drawn every 30 min for a period of 90 min after a single dose of the extract(s) was administered. Throughout the protocol time course, volunteers were advised to rest. Water was permitted to be consumed ad libitum. Immediately after collection, blood samples were gently inverted, aliquoted, snap frozen and kept at −70° C. until further use. Serum samples were collected upon clot formation after centrifugation. Serum was aliquoted, snap frozen and kept at −70° C. until use.

Blood Gas Determination:

For the determination of blood gases, finger blood samples were analyzed with a clinical blood gas analyzer (i-STAT Portable Clinical Blood Analyzer). Aliquots (100 ul) of blood were taken by finger puncture and collected in 100 uL Heparin-sulfate capillary tubes (Fisher Scientific). Blood was loaded in CG4+Cartridges (Abbot Laboratories, NJ, USA) for pH, PCO2, PO2, TCO2, HCO3, BEecf, sO2 and lactate determination. Blood was collected at baseline (T0) and subsequent samples were collected every 30 min (T3, T60, T90) post treatment.

Notably, experiments following the above procedures (details not shown here) have shown that the single dose treatment with compositions/extract(s) presented herein do not affect blood gases in a statistically significant manner.

ATP Detection and Quantification:

ATP concentration was determined using an ATP Assay Kit (Calbiochem, San Diego, Calif., USA) with a modification to the original method. Briefly, 10 µL blood and 100 µL ATP nucleotide-releasing buffer, containing 1 µL, luciferase enzyme mix were added to each well and immediately placed on a luminometer (LMaX, Molecular Devices; Sunnyvale Calif., USA) and a kinetic assay was read at 470 nm for 15 min at 3 min intervals. Relative Light Units (RLU) were recorded and ATP concentrations determined in comparison to an ATP standard curve.

Experiments following the above procedures (blood was collected at time 0, 30, 60 and 90 minutes, diluted in nucleotide releasing buffer and assayed for total ATP. Concentration was estimated based on a Standard Curve and calculated as % change over time 0 (T0). T1 represents average values of T30 and T60 and T2 represents T90) have shown that the single dose treatment with compositions/extract(s) presented herein increase ATP in vivo, typically by at least 10%, and more typically at least 13%.

Reactive Oxygen Species (ROS) Detection:

Reactive oxygen species (ROS) was detected by using a cell based ROS assay kit (Cell Biolabs, San Diego, Calif., USA) which is designed to detect ROS in media through cell leakage. However, with modifications to the original method, ROS was detected in lysed human blood. Briefly, 10 µL of diluted whole blood (1:100 in PBS) was mixed with 100 µL 2',7'-Dichlorodihydrofluorescein diacetate (DCFH-DA) 1× in PBS in a Nunc clear bottom black plate (Rochester, N.Y. USA). This mixture was immediately placed in a fluorescence spectrophotometer (Molecular Devices, Sunnyvale, Calif., USA) and a kinetic assay was run, recording Excitation/Emission (Ex/Em) at 480/530 nm for 45 min at 2 min intervals. ROS concentration was determined by comparison to a 2',7'-Dichlorodihydro-fluorescein (DCF) Standard Curve. A non-treated blood sample was used as control.

Experiments following the above procedures (details not shown here) have shown that the single dose treatment with compositions/extract(s) presented herein did not lead to a statistically significant increase in reactive oxygen or hydroxy species.

Oxygen Utilization of Cells In Vitro:

Contemplated compositions or extract(s) were used in a commercially available test format (Luxcel Biosciences, catalog number: MitoXpress-Xtra-KI) following the manufacturer's recommendations. More specifically, the MitoExpress assay was used in this study to monitor oxygen utilization by treated cells. This assay is based on oxygen-sensitive fluorescent probe. At high concentration of oxygen in water phase, fluorescent signal of the probe is measured by Relative Fluorescent Units (RFU). When oxygen is utilized, RFU is increasing. In this experimental set up, cultivated cells were treated with contemplated compositions/extract(s) or water as control at indicated doses. RFU was measured during 1 hour. Presented data were average measurements collected after 1 hour of exposure to compositions/extract(s). Cells were cultivated in 96-well plate for 24 hrs, washed, and exposed to fresh medium (control) or medium supplemented with compositions/extract(s) at appropriate dilutions.

In a second set of experiments, peripheral blood cells were isolated from healthy subjects using CPT tubes. After isolation, 2 million cells were suspended in culture buffer with or without compositions/extract(s). Oxygen utilization (RFU) was followed for 60 minutes. The data reflect oxygen utilized after one hour of treatment with compositions/extract(s).

Experiments following the above procedures (data not shown here) have shown that the compositions/extract(s) presented herein stimulate utilization of oxygen by cells in vitro in a dose-dependent manner under the described experimental conditions. For example, the compositions/extract(s) significantly increased oxygen utilization by Hepa 1c liver cells up to 50% and even higher at relatively low doses (typically below 1%). In comparison, the negative control (water) failed to show increased oxygen utilization under the same experimental conditions. Further experimental work (data not shown) indicated that compositions/extract(s) increased oxygen utilization in human peripheral blood cells that had been freshly collected from healthy human subjects. For example, contemplated compositions/extract(s) increased oxygen utilization up to 20% (and even higher) at low dosages after the first hour of the treatment. At doubled dose, oxygen utilization increased up to 35% under the same experimental conditions. These results show that the stimulatory effect of compositions/extract(s) on oxygen utilization is not limited to liver cells Hepa 1c, but that the compositions/extract(s) are also suitable for stimulation of oxygen utilization in normal human cells.

Mitochondrial Activity of Contemplated and Exemplary Compositions:

The following experiments were performed to establish stimulatory effect of contemplated compositions on oxygen metabolism in human cells as measured by OCR (Oxygen Consumption Rate) and ECAR (Extracellular Acidification Rate). Testing was performed using Seahorse technology in order to measure real-time changes in oxygen consumption by freshly isolated human peripheral blood cells. Additionally, the same technology was used to measure acidification rate, (an indicator of lactic acid production by cells treated with tested samples). Increases in extracellular level of lactic acid production under these experimental conditions are correlated with increased glucose utilization via glycolysis rather than oxidative phosphorylation.

All results were generated on freshly isolated blood cells from different and randomly selected healthy and fasted donors. Internal Controls: FCCP and oligomycin, two common drugs used in research on mitochondria, were used in each experiment to confirm accuracy of testing. FCCP stimulates cells to use more oxygen; however, glycolysis remained the main process to generate ATP and energy. Therefore, treatment of cells with FCCP results in high values for OCR and ECAR. By average, FCCP causes 397% increase in OCR and treatment with oligomycin results by average in 86% inhibition of OCR. These two values were used as positive and negative controls, respectively, in order to ensure quality of test, viability and metabolic functionality of fresh human blood cells. Oligomycin inhibits oxygen metabolism. In presence of this substance, cells generate ATP/energy mainly via glycolysis. Therefore, treatment of cells with oligomycin under these experimental conditions result in high ECAR values. To ensure quality of human blood cells, blood was collected directly into Cell Preparation Tube with Sodium Citrate, Becton Dickinson Inc. Peripheral blood cells were isolated during 45 minutes following Protocol provided by Becton Dickinson. Blood cells were cultivated during each experiment in Seahorse media supplemented with 5 mM of glucose. Glucose concentration was adjusted from 11 mM to 5 mM to avoid testing of samples under hyperglycemic conditions (typically glucose at concentration lower than 95 mg/dl).

Experiments following the above procedures have shown that the compositions/extract(s) presented herein increase the "OCR/ECAR index" (obtained by dividing OCR % increase or decrease compared to Sigma Water control by the ECAR % change over the same control), where the OCR increase is at least 10% over control, more typically at least 25% over control, and most typically at least 40% over control. A typical experimental result for multiple samples and concentrations of the extract(s) is graphically depicted in FIG. 1. As can be readily taken from FIG. 1, oxygen consumption rate increased without concomitant increase in extracellular acidification, indicating an improved oxygen utilization.

Figure 2:
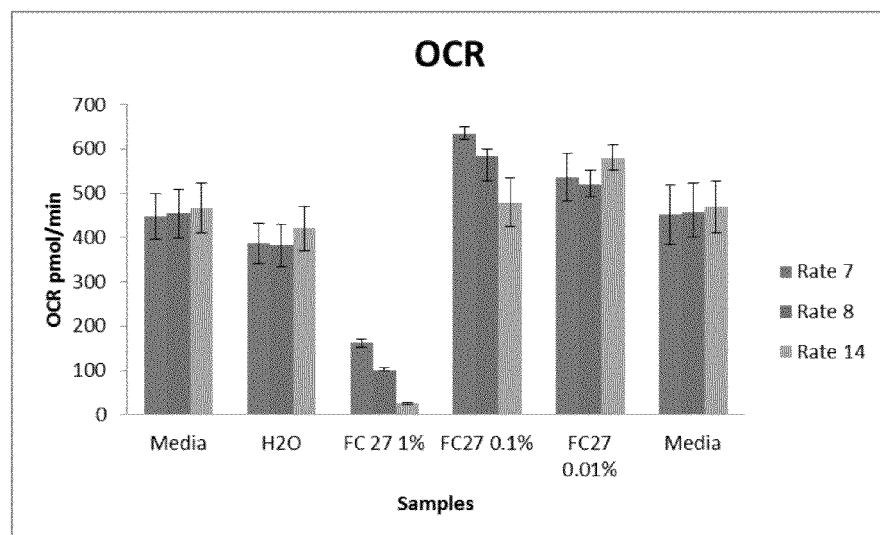
FIG. 2 is a graph depicting changes in oxygen consumption rate of cells exposed to contemplated compositions.

In still further experiments, a commercially available apple extract (VDF Futureceuticals, FC27) was tested to establish that the extract increases Oxygen Consumption Rate (OCR) in freshly isolated peripheral blood cells. Cells were isolated from healthy fasted subject, and treated with apple extract at indicated dose. The results in FIG. 2 below show that apple extract increased OCR compared to H2O control (vehicle) at dose 0.1 and 0.01%. Under the same experimental conditions, treatment of the cells with apple extract at dose 1% resulted in significant reduction of OCR value. Rate 7, 8 and 14 represent time-points: 4, 8 and 32 minutes after the treatment, respectively.

Figure 3:
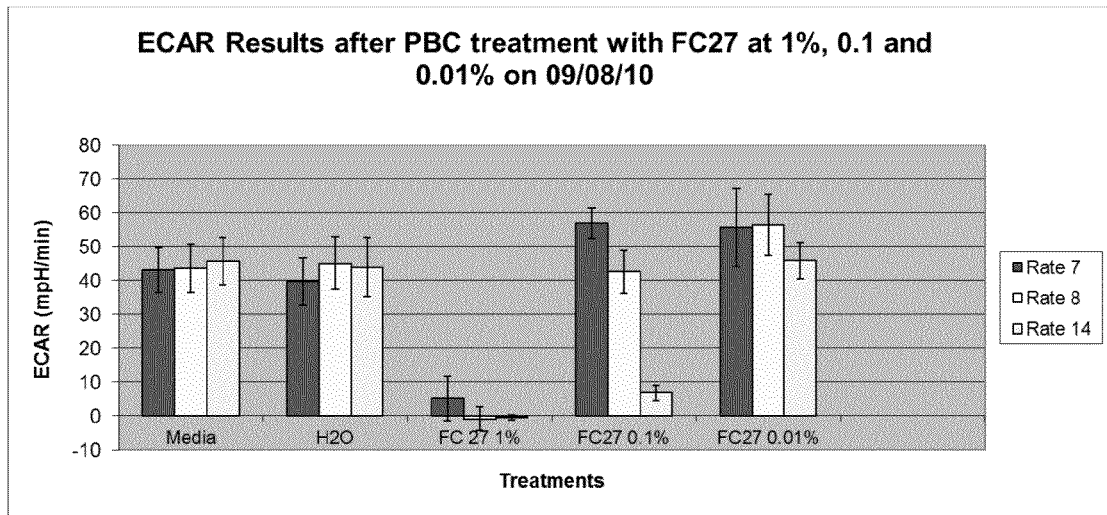
FIG. 3 is a graph depicting changes in extracellular acidification rate of cells exposed to contemplated compositions.
Figure 4:
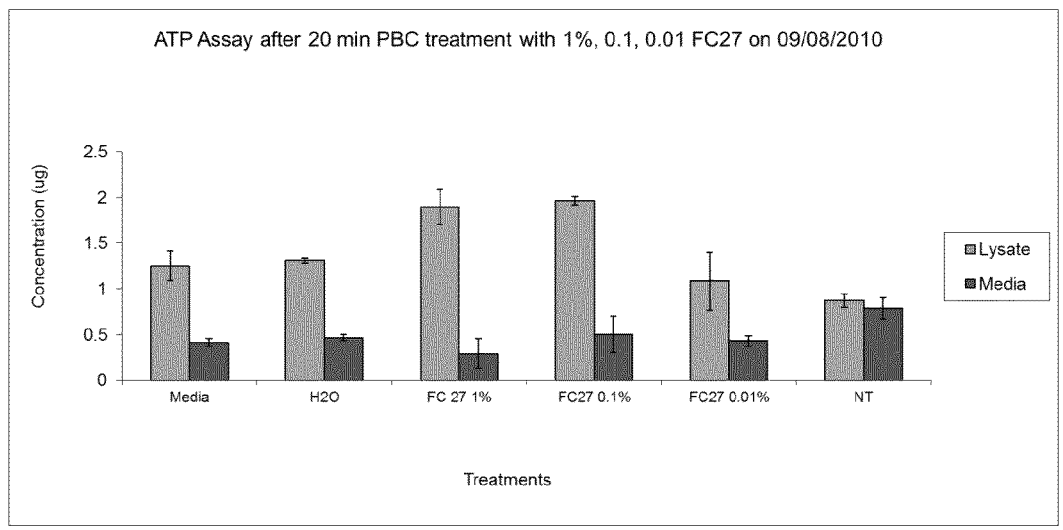
FIG. 4 is a graph depicting changes in ATP production of cells exposed to contemplated compositions.

Additionally, the same extract was also tested for the capability to influence ECAR. Here, the apple extract (FC27) reduced ECAR at dose 1% and 0.1%, but not at dose 0.01%. These results indicate that acidification of extracellular environment due to release of lactate or leak of protons is reduced or not changed, respectively, in FIG. 3. Moreover, the apple extract was also tested for stimulation of ATP generation. More specifically, the extract was shown to stimulate human fresh blood cells to generate more ATP at a dose of 1% and 0.1% as can be seen from FIG. 4 below. This result indicates that FC27 at dose 1% does not stimulate toxic effect (reduced OCR and ECAR) since cells can produce ATP (intracellular ATP in cell lysate) and extracellular ATP (media) remain unchanged.

Figure 5:
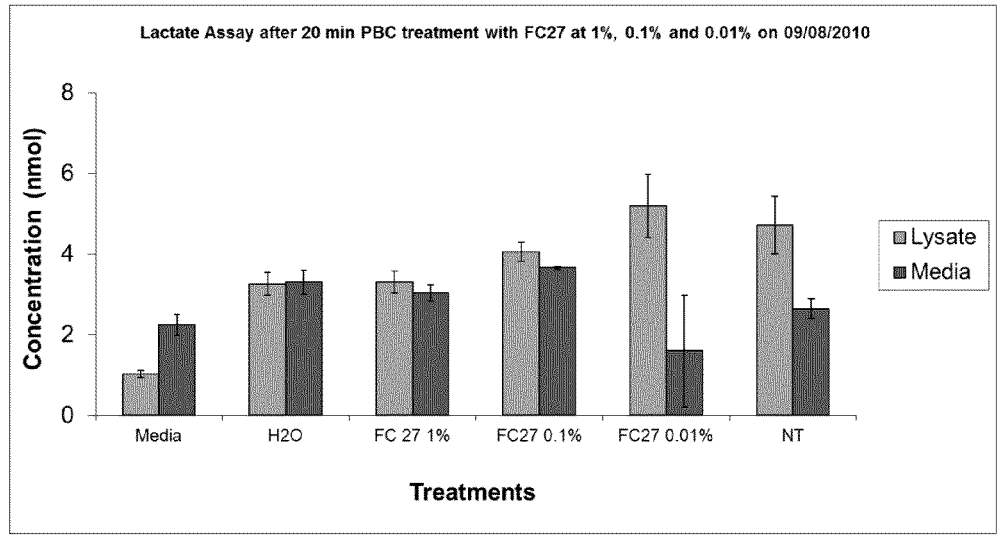
FIG. 5 is a graph depicting changes in lactate production of cells exposed to contemplated compositions.

Lastly, the apple extract also showed minor effect on intracellular and extracellular level of lactate at dose 0.001% whereas at dose 0.1 and 1.0% of FC27, level of lactate remained unchanged as can be seen from FIG. 5 below. Thus, the results indicate that apple extract may affect mitochondrial metabolism by stimulating ATP production without adversely affecting lactate production.

Follow-Up Study

In a follow-up study, the inventor also discovered that contemplated compositions and formulations increased ATP in vivo upon oral administration, and dramatically increased ATP in muscle tissue. In short, oral placebo was administered on the first day of testing followed by a single, 150 mg dose of elevATP™ (ancient peat-based bioinorganic material blended with apple extract polyphenols; commercially available from FutureCeuticals, 2692 N. State Rt. 1-17, Momence, Ill. 60954) on the second day. Blood was collected immediately prior to treatment, 60 and 120 minutes after ingestion. Whole blood ATP, plasma ATP, hemoglobin, blood lactate, and blood glucose levels were determined at each point. A muscle biopsy was performed on one resting study subject before, and 60 and 120 minutes after, a single dose of elevATP™. elevATP™ increased whole blood levels of ATP by 40% after 60 minutes (p<0.0001) and by 28% after 120 min (p=0.0009) versus baseline, pre-supplementation levels. ATP plasma levels did not increase after elevATP™ administration under these experimental conditions. Intramuscular ATP levels from biopsy of one patient increased significantly at 60 and 120 minutes after ingestion of elevATP™ and reached higher levels than ATP measured in whole blood. These results indicate that elevATP™ increases intracellular ATP in blood cells, confirming results from a previous study and suggest that it may increase ATP in muscle tissue.

elevATP™ was provided by FutureCeuticals, Inc., Momence, Ill. USA. Dulbecco's phosphate buffered saline (PBS), phenyl methane-sulfonyl-fluoride (PMSF), dimethyl sulfoxide (DMSO), leupeptin, EDTA, NaCl, nitrobenzyl thioinosine (NBTI), KCl, tricine, forskolin, isobutylmethylxanthine (IBMX) and water were purchased from Sigma Chem. Co. (St Louis, Mo., USA). ATP stabilizing solution was prepared as described by Gorman et al. (118 mmol NaCl, 5 mmol KCl, 40 mmol tricine buffer, 4.15 mmol EDTA, 5 nmol NBTI, 10 µmol forskolin and 100 µmol IBMX, at pH 7.4 adjusted with 2 mol/L KOH).

Low protein binding microtubes were obtained from Eppendorf (Hauppauge, N.Y., USA) and RC DC Protein Assay Kit II was obtained from Bio-Rad (Palo Alto, Calif., USA). ATP-luciferase assays were obtained from Calbiochem (San Diego, Calif., USA). Heparin capillary blood collection tubes were obtained from Safe-T-Fill® (Ram Scientific Inc. Yonkers, N.Y.). A portable gas meter and CG8+ cartridges were obtained from Abbott Laboratories (Abbott Park, Ill., USA). Total hemoglobin quantification ELISA kits were obtained from MyBiosource (San Diego, Calif., USA). Accutrend® Lactate Point of Care and BM-Lactate Strips® were obtained from Roche (Mannheim, Germany). Accu-Chek® Compact Plus glucometer and Accu-Chek® test strips were obtained from Roche Diagnostics (Indianapolis, Ind., USA).

This clinical case study was conducted according to guidelines laid out in the Declaration of Helsinki. All procedures involving human subjects were approved by the Institutional Review Board at Vita Clinical S.A. Avenida Circunvalacion Norte #135, Guadalajara, JAL, Mexico 44 270 (study protocol no. ABC-13-09-ATP). Twenty subjects were selected to participate. They were generally healthy, and free of rhinitis, influenza, and other acute infections. 12 female and 8 male subjects were selected, with ages ranging from 22 to 35 years and BMI ranging from 24.1 to 30 kg/m$^2$. Exclusion criteria included diagnosis of diabetes mellitus, allergies to dietary products, use of anti-inflammatory drugs, analgesics, statins, diabetic drugs, anti-allergy medicines, multivitamins, and use of supplements within 15 days of the start of the study. All participants gave written, informed consent before any experimental procedure was performed.

Enrolled participants were instructed not to eat for 12 h prior to the initial blood draw. Resting subjects were given an empty capsule as placebo on Day 1 of the study and 150 mg of encapsulated elevATP™ on Day 2. 250 mL of water was administered with the capsules each day. 200 µL of blood was collected by finger puncture and placed in Safe-T-Fill® Capillary blood collection tubes (Ram Scientific Inc. Yonkers, N.Y.). Blood samples were collected immediately prior to test capsule administration and at 60 and 120 minutes after ingestion.

One hundred µl of blood was transferred to low-protein binding tubes (Eppendorf, Hauppauge, N.Y., USA) immediately after collection. An equal volume of ATP stabilizing solution was added to each tube. Tubes were gently mixed by inversion and centrifuged at 13,000 g for 3 min to pellet cells. Supernatant was transferred to a clean tube and spun again at 13,000 g for 3 min. The supernatant was then snap frozen and stored at −80° C. prior to ATP analysis.

Blood ATP or plasma ATP concentrations were determined using ATP Assay Kits (Calbiochem, San Diego, Calif., USA) with a modification to the original method. Briefly, 10 µL of lysed blood or plasma was loaded onto a white plate (Corning® Fisher Scientific, Waltham, Mass., USA). 100 µL of ATP nucleotide-releasing buffer containing 1 µL luciferase enzyme mix was added and the plate was immediately placed on a illuminometer (LMaX, Molecular Devices; Sunnyvale Calif., USA). Readings were performed for 15 min at 3 min intervals, at 470 nm. Relative Light Units (RLU) were recorded and ATP concentrations were determined using a standard ATP curve.

Hemoglobin levels in plasma were determined using a double sandwich ELISA (MyBiosource, San Diego, Calif., USA), concentration was determined comparing to a standard curve, according to the manufacturer's instructions. Plasma samples collected with the ATP stabilizing solution were used for this analysis.

Blood lactate was measured using an Accutrend® Lactate Point of Care (Roche, Mannheim, Germany) and BM-Lactate Strips® (Roche, Mannheim, Germany). Fifteen µL of blood was loaded onto the strip and lactate levels were read according to the manufacturer's instructions. Glucose was measured using an Accu-Chek® Compact Plus glucometer (Roche Diagnostics, Indianapolis, Ind., USA) and Accu-Chek® test strips (Roche Diagnostics, Indianapolis, Ind., USA). Glucose was read according to the manufacturer's instructions. Lactate and glucose levels were determined at every collection time point.

For each result obtained from the described assays, each subject was normalized to their own value measured at baseline (T0), before ingestion of elevATP™ or placebo. Levels of each assay at 60 (T60) and 120 (T120) minutes after treatment were compared within experimental groups to the baseline and between experimental groups using a paired t-statistic test. Descriptive analyses were run in GraphPad® to derive the mean and standard deviation of each group.

For the muscle biopsy, one twenty two-year old healthy subject, with a BMI of 24.5 was recruited, following the same selection criteria as described for the clinical crossover study. This clinical case study was conducted according to guidelines laid out in the Declaration of Helsinki. This procedure was approved by the Institutional Review Board at Vita Clinical S.A. Avenida Circunvalacion Norte #135, Guadalajara, JAL, Mexico 44 270 (study protocol no. ABC-NCI-13-01-ATP-Mus1). The study subject was selected from the group of subjects enrolled for whole blood ATP measurement, as described above. This subject was fasted and resting during this experiment. Biopsy was performed using aseptic technique. An antiseptic solution (Isodine) was applied to the medial region of the arm, over the right biceps. An 18 g needle was used to infiltrate the skin with 5 cc lidocaine. A skin incision was made using a 3 mm skin biopsy punch. Subcutaneous tissue was bluntly divided, allowing resection of 3 mm$^2$ of biceps muscle using Metzenbaum scissors. Muscle tissue from the biceps was collected before, and also 60 and 120 minutes after, ingestion of elevATP™. Muscle tissue was deposited in a 50 ml conical tube and frozen using liquid nitrogen prior to further processing needed for measuring of ATP.

Frozen muscle tissue was added to a glass tissue grinder (Fisher Scientific, Chino, Calif., USA) containing 200 µL ice cold ATP stabilizing solution, as previously described by Gorman et al. Tissue was mechanically ground and transferred to a low-protein binding microtube (Eppendorf, Hauppauge, N.Y., USA). The sample was centrifuged for 5 min at 10,000 g and supernatant was used for ATP quantification. ATP concentration was determined using an ATP Assay Kit (Calbiochem, San Diego, Calif., USA) with a modification to the original method, as previously described.

Hemoglobin levels were also determined in muscle tissue lysates, using a double sandwich ELISA (MyBiosource, San Diego, Calif., USA), according to the manufacturer's instructions. Tissue samples homogenized in ATP stabilizing solution described by Gorman et al. were used for this analysis.

Twenty healthy subjects were recruited for this placebo-controlled, crossover study. Subjects fasted overnight and were then given an empty capsule as placebo (Day 1). Blood was collected at baseline (before treatment) and 60 min (T60) and 120 min (T120) after treatment. Subjects fasted overnight, prior to Day 2, when a single capsule containing 150 mg of elevATP™ was administered to each subject. Blood was obtained as previously described. Blood ATP and glucose, and plasma ATP and hemoglobin levels were also determined.

Figure 6:
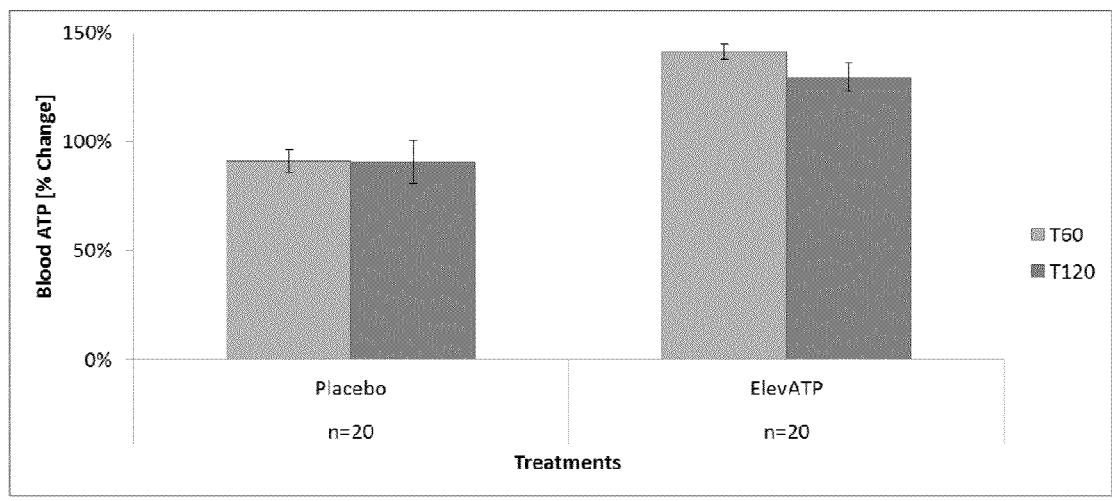
FIG. 6 is a graph depicting changes in whole blood ATP levels upon oral administration of contemplated compositions.

A single dose of 150 mg elevATP significantly increased blood ATP by 40% at 60 minutes (p<0.0001) and 28% at 120 min (p=0.0009) as compared to baseline ATP level at T0 (FIG. 6). Here, the effect of elevATP™ on blood ATP levels is shown. elevATP™ significantly increased blood ATP levels by 40% at T60 (p<0.0001) and 28% at T120 (p=0.0009) over initial baseline T0 values. Data are presented as Mean+/−SE. n=20.

Figure 7:
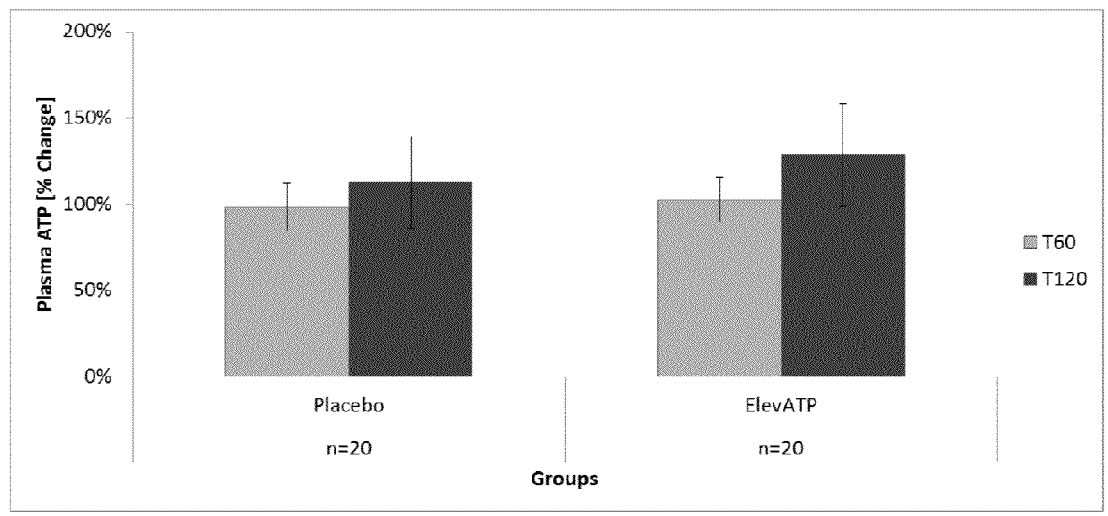
FIG. 7 is a graph depicting changes in plasma ATP levels upon oral administration of contemplated compositions.

Plasma ATP levels were measured using 10 µL of plasma in a luciferase-based assay. There was no significant increase in ATP level at T60 (p=0.83) or T120 (p=0.69) in patients treated with elevATP™ (FIG. 7). The figures depicts Plasma ATP levels after treatment with elevATP™. Data is presented as Mean+/−SE, Data are presented as % change over baseline T0. n=20. No change in plasma ATP level was seen after treatment with placebo.

Figure 8:
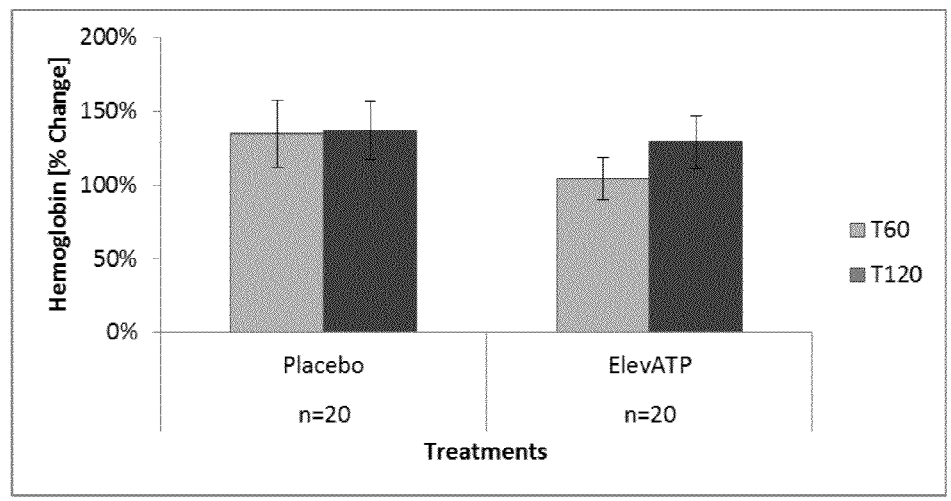
FIG. 8 is a graph depicting changes in plasma hemoglobin levels upon oral administration of contemplated compositions.

Hemoglobin levels were determined in all plasma samples in order to ensure that mechanical disruption of erythrocytes did not affect plasma ATP levels. The placebo group had an increase in plasma hemoglobin of 34% at T60 and 37% at T120 on day 1, compared to the T0 baseline (FIG. 8). The figure depicts Hemoglobin levels after treatment with elevATP™. There was a 4% increase at T60 and 28% increase at T120. There were no statistical differences when compared to placebo. Data are presented as Mean+/−SE, n=20. On day 2, after treatment with elevATP™, there was an increase in plasma hemoglobin level of 4% at T60 and 28% at T120, compared to the new T0 baseline. There were no statistically significant differences in placebo and elevATP™ treatments at T60 (p=0.29) and T120 (p=0.76).

Blood glucose levels were monitored after treatment with placebo (Day 1) and after elevATP™ (Day 2), as previously described. There were no significant differences in blood glucose levels between treatments at T60 (p=0.57) or T120 (p=0.59) in the 20 patients examined. Blood lactate levels remained unchanged after placebo (Day 1) or elevATP™ (Day 2) administration. The difference between treatments was not significant either at T60 (p=0.61) or T120 (p=0.44).

Figure 9:
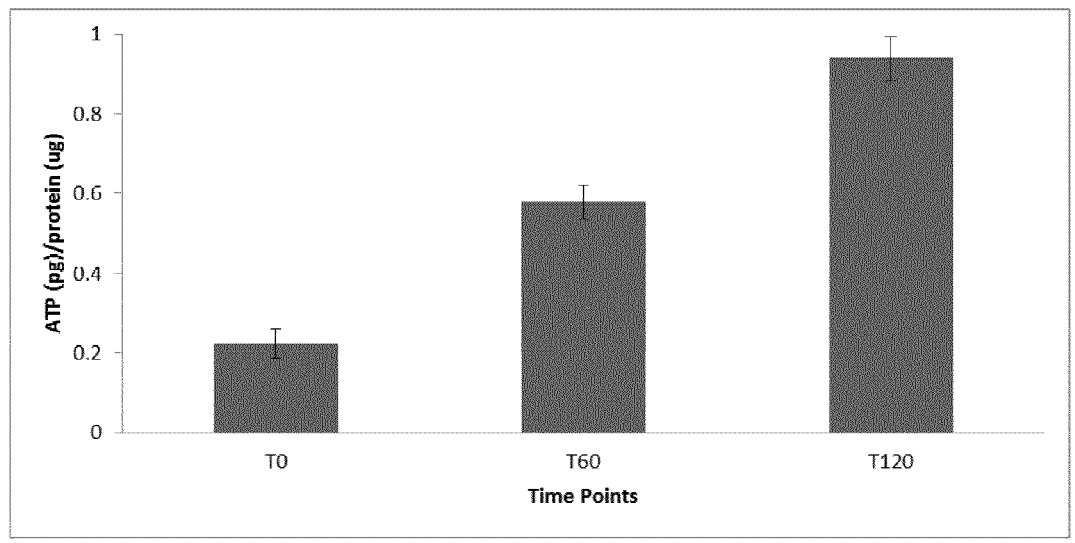
FIG. 9 is a graph depicting changes in ATP levels in muscle tissue upon oral administration of contemplated compositions.
Figure 10:
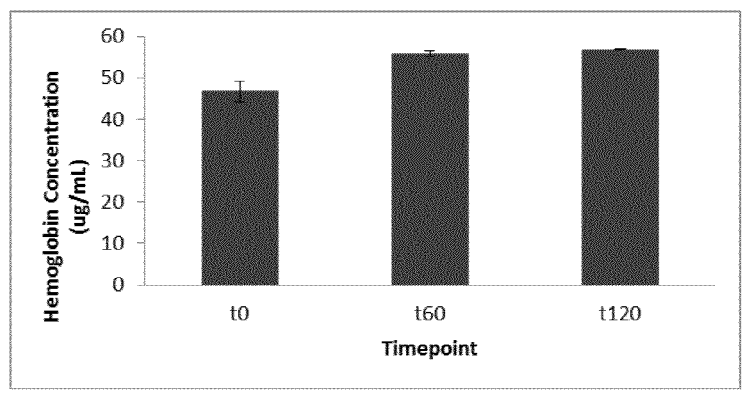
FIG. 10 is a graph depicting changes in hemoglobin in muscle tissue upon oral administration of contemplated compositions.

Biceps muscle levels of ATP were determined before and after administration of elevATP™. 210 pg ATP per mg protein was detected at T0, prior to treatment (FIG. 9). The figure depicts ATP levels in muscle tissue after treatment with elevATP™. ATP levels increased significantly after treatment. Data is presented as mean+/−SE of 4 determinations. ATP level increased in muscle biopsy tissue to 590 pg/mg protein at 60 minutes and 910 pg/mg protein at 120 minutes. Hemoglobin was also quantified in muscle biopsy lysates in order to ensure that mechanical disruption of the tissue did not affect ATP levels (FIG. 10). The figure illustrates Hemoglobin levels in muscle tissue lysates before and after treatment with elevATP™. Hemoglobin increased 19% over baseline at T60 and 22% at T120. Data is presented as Mean+/−SD of 3 determinations. Hemoglobin levels did not increase after treatment.

Thus it should be appreciated that contemplated compositions, and especially a complex trace element composition (e.g., elevATP™) appears to selectively and acutely increase ATP levels within the cellular component of blood. In contrast, ATP levels in cell-free plasma remained unchanged following elevATP™ ingestion. The inventor verified the integrity of erythrocyte cell membranes by quantifying hemoglobin concentrations in plasma. This suggests that ATP did not originate from ruptured red blood cells. Likewise, the inventor found no changes in plasma ATP levels after treatment with elevATP™, suggesting that it is unlikely that elevATP™ affects extracellular ATP levels. The lack of changes in blood glucose and lactate levels suggests that ATP originated from blood cells with mitochondria, such as platelets and while blood cells.

As presented here, muscle tissue, which is rich in mitochondria, exhibited a substantial increase in ATP levels after elevATP™ ingestion. The data also show that elevATP™ did not increase reactive oxygen species, despite increasing ATP levels.

Trace Element Study

To further investigate the nature of the mineral component, the inventor also discovered that not all humic shale preparations were equally potent in their ATP increasing effect, and some of the preparations were even inhibitory. In the below shown data, humic shale material was obtained from the same geologic location, but from different vertical strata. In the below set of data, the different strata were separated by 2 ft increments. N881.1 is a commercially available mineral composition (FutureCeuticals, 2692 N. State Rt. 1-17, Momence, Ill. 60954), ElevATP is combination of Elemin™ (N881.1) with apple extract (FC27).

| | Ex Vivo at 0.001 wt % | | ATP determined In Clinico at 150 mg | | | |
|---|---|---|---|---|---|---|
| | Change over control (%) | SD ± | T60 % | T60 SD ± | T120 % | T120 SD ± |
| ElevATP | 116% | 4% | 146% | 47% | 164% | 24% |
| Stratum 1 | 22% | 6% | N/D | N/D | N/D | N/D |
| Stratum 2 | 67% | 17% | N/D | N/D | N/D | N/D |
| Stratum 3 | 48% | 4% | N/D | N/D | N/D | N/D |
| Stratum 4 | 52% | 8% | 72% | 14% | 59% | 20% |
| Stratum 5 | 238% | 16% | 122% | 10% | 133% | 5% |
| Stratum 6 | 120% | 73% | 92% | 22% | 76% | 14% |
| Stratum 7 | 73% | 18% | 110% | 88% | 91% | 51% |
| Stratum 8 | 205% | 49% | 97% | 21% | 149% | 70% |
| Stratum 9 | 128% | 17% | N/D | N/D | N/D | N/D |
| Stratum 10 | 67% | 22% | N/D | N/D | N/D | N/D |
| Stratum 11 | 86% | 19% | N/D | N/D | N/D | N/D |
| N881.1 | 249% | 95% | 113% | 6% | 120% | 7% |

As can be seen from the in vitro and in vivo data, different strata provided significantly different activities where extracts were prepared from these strata. Therefore, it should be appreciated that compounds, compositions, and methods for increase of ATP levels in whole blood in vitro and in vivo can be rationally designed. Most preferably, mineral compositions can be tested in vitro using whole blood as described in the experimental section above and validated in vivo, following the same protocols as also described above. Thus, especially contemplated compositions for ATP increase in whole blood and/or muscle tissue will include one or more elements (typically (trace) minerals in ionic and/or elemental form) that are demonstrated to have activity for increasing ATP levels in whole blood or muscle tissue (or other mitochondria containing tissue).

For example, a designed formulation may be based on differential enrichment and/or presence of certain elements as can be taken from Table 2 below, where data with light grey highlight show differences between active and inactive fraction, data with medium grey highlight show enrichment after extraction (relative to crude ore fraction), and data with dark grey highlight show reduction in elemental content after extraction (relative to crude ore fraction).

TABLE 2

| Metal by ICP-MS | ORE ppm | Active fraction ppm | Inactive Fraction ppm |
|---|---|---|---|
| Aluminium | 8500 | 7700 | 28000 |
| Antimony | 0.12 | ND | ND |
| Arsenic | 7 | 0.09 | 0.16 |
| Barium | 88 | 0.39 | 0.23 |
| Beryllium | 0.54 | 1.7 | 4.2 |
| Bismuth | 0.38 | ND | ND |
| Boron | 9.6 | 41 | 14 |
| Bromine | ND | ND | 15 |
| Cadmium | 0.49 | 11 | 9.5 |
| Calcium | 25000 | 5600 | 20000 |

TABLE 2-continued

| | | | |
|---|---|---|---|
| Cerium | 40 | 7.9 | 7.7 |
| Cesium | 1.8 | 0.03 | 0.05 |
| Chromium | 7.8 | ND | 14 |
| Cobalt | 9.7 | 60 | 130 |
| Copper | 22 | 1.3 | 4.2 |
| Dysprosium | 2.8 | 8.5 | 30 |
| Erbium | 1.1 | 4.3 | 14 |
| Europium | 0.84 | 1.5 | 4.5 |
| Gadolinium | 4 | 9.2 | 30 |
| Galium | 3.9 | 0.31 | 0.36 |
| Germanium | 3.3 | 0.92 | 1 |
| Gold | ND | ND | ND |
| Hafnium | 0.61 | 0.07 | 0.18 |
| Holmium | 0.48 | 1.7 | 5.9 |
| Iodine | 0.12 | 0.03 | 0.08 |
| Iridium | ND | ND | ND |
| Iron | 24000 | 20 | 87 |
| Lanthanum | 14 | 2.7 | 1.1 |
| Lead | 17 | ND | ND |
| Lithium | 24 | 380 | 390 |
| Lutetium | 0.09 | 0.34 | 0.94 |
| Magnesium | 7300 | 120000 | 89000 |
| Manganese | 92 | 770 | 1600 |
| Mercury | 0.03 | ND | ND |
| Molybdenum | 7 | ND | ND |
| Neodymium | 21 | 8.2 | 8.8 |
| Nickel | 28 | 300 | 480 |
| Niobium | 0.29 | ND | ND |
| Osmium | ND | ND | ND |
| Palladium | 0.03 | 0.09 | 0.25 |
| Phosphorus | 630 | 9.3 | 25 |
| Platinium | ND | ND | ND |
| Potassium | 2100 | 880 | 700 |
| Praseodymium | 5.6 | 1.3 | 1 |
| Rhenium | 0.03 | 0.34 | 0.3 |
| Rhodium | ND | ND | ND |
| Rubidium | 20 | 3.5 | 5.4 |
| Ruthenium | ND | ND | ND |
| Samarium | 3.9 | 5.3 | 12 |
| Selenium | 2.5 | 3.5 | 4.5 |
| Silver | 0.1 | ND | ND |
| Sodium | 1100 | 31000 | 13000 |
| Strontium | 150 | 641 | 14 |
| Tantalum | ND | ND | 0.03 |
| Terbium | 0.54 | 1.4 | 5 |
| Tellurium | 0.17 | ND | ND |
| Thalium | 0.49 | 0.42 | 0.16 |
| Thorium | 8.4 | 0.03 | 0.28 |
| Thulium | 13 | 0.49 | 1.5 |
| Tin | 0.51 | ND | ND |
| Titanium | 36 | 0.3 | 0.3 |
| Tungsten | 0.04 | 0.04 | 0.1 |
| Uranium | 1.6 | 0.37 | 0.86 |
| Vanadium | 12 | ND | ND |
| Ytterbium | 0.68 | 2.5 | 7.2 |
| Yttrium | 14 | 64 | 190 |
| Zinc | 87 | 160 | 660 |
| Zirconium | 3.2 | 0.17 | 0.31 |

Therefore, exemplary mineral compositions may comprise one or more enriched minerals (e.g., Beryllium, Boron, Cadmium, Cobalt, Dysprosium, Erbium, Europium, Gadolinium, Holmium, Lithium, Lutetium, Magnesium, Manganese, Nickel, Rhenium, Samarium, Sodium, Terbium, Ytterbium, Yttrium, and/or Zinc), or minerals that are preferentially found in the active strata relative to inactive or inhibitory strata (e.g., Boron, Lanthanum, Magnesium, Sodium, and/or Strontium). On the other hand, contemplated compositions may also include minerals that were preferentially removed relative to the inactive or inhibitory strata (e.g., Aluminum, Beryllium, Calcium, Cobalt, Copper, Erbium, Europium, Gadolinium, Hafnium, Holmium, Iron, Lutetium, Manganese, Nickel, Palladium, Phosphorus, Samarium, Terbium, Thorium, Thulium, Ytterbium, Yttrium, and/or Zinc).

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of increasing adenosine triphosphate (ATP) in a tissue having mitochondria, comprising:
   providing a mineral composition having a pharmaceutically or nutritionally acceptable carrier in combination with a humic shale extract, wherein the humic shale extract comprises a plurality of distinct inorganic trace elements in ionic or elemental form;
   wherein the plurality of inorganic trace elements in the composition are in an amount effective to increase ATP quantities in a tissue at least 30% in 60 minutes after oral administration; and
   administering the mineral composition under a protocol demonstrated to increase the ATP in the tissue.

2. The method of claim 1 wherein the tissue having mitochondria is whole blood or muscle tissue.

3. The method of claim 1 wherein the trace elements are selected from the group consisting of Beryllium, Boron, Cadmium, Cobalt, Dysprosium, Erbium, Europium, Gadolinium, Holmium, Lithium, Lutetium, Magnesium, Manganese, Nickel, Rhenium, Samarium, Sodium, Terbium, Ytterbium, Yttrium, and Zinc.

4. The method of claim 1 wherein the trace elements are selected from the group consisting of Boron, Lanthanum, Magnesium, sodium, and Strontium.

5. The method of claim 1 wherein the trace elements are selected from the group consisting of Aluminum, Beryllium, Calcium, Cobalt, Copper, Erbium, Europium, Gadolinium, Hafnium, Holmium, Iron, Lutetium, Manganese, Nickel, Palladium, Phosphorus, Samarium, Terbium, Thorium, Thulium, Ytterbium, Yttrium, and Zinc.

6. The method of claim 1 wherein the humic shale extract comprises an aqueous extract of humic shale.

7. The method of claim 6 wherein the extract is a dried extract.

8. The method of claim 1 wherein the mineral composition further comprises a fruit extract that comprises polyphenolic compounds.

9. The method of claim 8 wherein the fruit extract is an extract of an apple fruit or an extract of a skin of an apple.

10. A method of identifying a mineral composition as increasing ATP production in a tissue, the method comprising:
    combining a mineral composition with whole blood to form an incubation mixture;
    the mineral composition having a pharmaceutically or nutritionally acceptable carrier in combination with a humic shale extract of an ATP stimulating stratum of humic shale from a geologic location, wherein the humic shale extract comprises a plurality of distinct inorganic trace elements in ionic or elemental form;
    lysing the whole blood in the incubation mixture, and combining the lysed whole blood with a luciferase to form a reaction mixture; and
    measuring light output of the reaction mixture, and comparing the light output against a standard, wherein increased light output over the standard is indicative of an increase of ATP production by the mineral composition.

11. The method of claim 10 wherein the mineral composition comprises at least one element selected from the group consisting of Beryllium, Boron, Cadmium, Cobalt, Dysprosium, Erbium, Europium, Gadolinium, Holmium, Lithium, Lutetium, Magnesium, Manganese, Nickel, Rhenium, Samarium, Sodium, Terbium, Ytterbium, Yttrium, and Zinc.

12. The method of claim 10 wherein the mineral composition comprises an aqueous extract of humic shale.

13. The method of claim 10 wherein the step of measuring is performed for at least 10 minutes.

* * * * *